United States Patent [19]

Fujita et al.

[11] 4,251,460
[45] Feb. 17, 1981

[54] PROCESS FOR PRODUCTION OF DIMETHYLFORMAMIDE

[75] Inventors: Takeyuki Fujita, Yokosuka; Masaru Suto; Kazumoto Ogura, both of Yokohama, all of Japan

[73] Assignee: Nitto Chemical Industry Co., Ltd., Tokyo, Japan

[21] Appl. No.: 105,370

[22] Filed: Dec. 19, 1979

[30] Foreign Application Priority Data

Dec. 27, 1978 [JP] Japan .............................. 53-160075

[51] Int. Cl.$^3$ ........................................... C07C 103/36
[52] U.S. Cl. ..................................... 564/132; 564/216
[58] Field of Search ........... 260/585 B, 583 N, 583 R, 260/583 J, 561 R

[56] References Cited

U.S. PATENT DOCUMENTS

| | | | |
|---|---|---|---|
| 2,071,301 | 2/1937 | Herold et al. | 260/585 B X |
| 2,079,580 | 5/1937 | Swallen | 260/585 B X |
| 2,085,785 | 7/1937 | Bottoms | 260/585 B X |
| 2,377,511 | 7/1945 | Olin | 260/585 B |
| 3,720,715 | 3/1973 | Nicholl | 260/583 J |

FOREIGN PATENT DOCUMENTS

| | | | |
|---|---|---|---|
| 410500 | 5/1934 | United Kingdom | 260/583 R |
| 421486 | 12/1934 | United Kingdom | 260/585 B |
| 422564 | 1/1935 | United Kingdom | 260/585 B |

OTHER PUBLICATIONS

Zabicky, "The Chemistry of Amides," p. 118 (1970).

*Primary Examiner*—John Doll
*Attorney, Agent, or Firm*—Sughrue, Rothwell, Mion, Zinn and Macpeak

[57] ABSTRACT

A process for producing dimethylformamide which comprises reacting methanol and ammonia to give methylamines, separating a dimethylamine-trimethylamine mixture from the methylamines, and reacting the dimethylamine-trimethylamine mixture with carbon monoxide to produce dimethylformamide.

12 Claims, 1 Drawing Figure

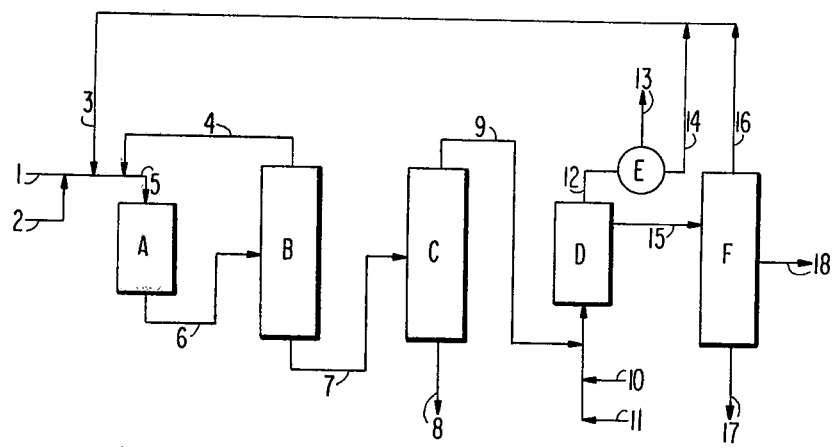

PROCESS FOR PRODUCTION OF DIMETHYLFORMAMIDE

BACKGROUND OF THE INVENTION

1. Field of the Invention

This invention relates to a process for the production of dimethylformamide. More particularly, it is concerned with a process for producing dimethylformamide which comprises reacting methanol and ammonia to form methylamines, separating a mixture of dimethylamine and trimethylamine from the methylamines, and reacting the mixture of dimethyamine and trimethylamine with carbon monoxide to produce dimethylformamide.

2. Description of the Prior Art

Dimethylformamide (hereinafter abbreviated "DMF") is widely used in many industrial applications, for example, as a solvent for artificial leather, urethane fibers, acryl fibers and various resins, and moreover, as a reaction solvent or reagent for a wide variety of organic syntheses.

For the production of such industrially useful DMF, there are two typical processes. One is based on the reaction of dimethylamine (hereinafter "DMA") and carbon monoxide, and the other is based on the reaction of DMA and methyl formate. In the latter process, however, methanol is an inevitable by-product and the reaction steps are complicated. Therefore, the former process is advantageously employed from the industrial standpoint.

In the production of DMF by the reaction of DMA and carbon monoxide, the starting material DMA should be of high purity for the reasons explained hereinafter.

The reaction of DMA and carbon monoxide is carried out in the presence of an alkali metal alcoholate catalyst. If DMA contains water, the alkali metal alcoholate reacts with the water and it is unfavorably consumed. As a result, the reaction of DMA and carbon monoxide does not proceed.

In addition, if DMA contains ammonia and other amines, various amides are by-produced during the synthesis of DMF. These by-produced amides are formamide, N-methyl formamide, N,N-dimethylacetamide and the like. Although their boiling points are higher than that of DMF, their stabilities to heat and water are inferior to that of DMF. In the purification of DMF, therefore, these amides are subject to thermal decomposition in the reboiler of a distillation column and so on, or to hydrolysis in the presence of a small amount of water. As a result, the decomposition products of these amides, i.e., ammonia and amines, formic acid, and the salts thereof are brought into the purification step of DMF. Thus, the purification step is made complicated.

DMF is required to be of high quality from the point of application. That is, it is required not only to be of high purity, but also to meet certain physical requirements. For example, when DMF is used as a polymerization solvent for the production of a polyurethane based artificial leather and synthetic fibers, the addition reaction rate of an active hydrogen compound, such as a polyol, with isocyanate is influenced by the quality of DMF. The addition reaction rate is high when the pH of DMF is high (pH=9 or more) according to the quantity of amines contained in DMF, whereas when DMF contains formic acid and so on, and its pH is low (pH=6 or less), the addition reaction rate is low.

Moreover, when DMF contains organic acid salts, the electric conductivity of DMF increases.

As described above, the physical properties of DMF are greatly influenced by the impurities contained therein. In practical use, therefore, DMF should be of high purity and high stability, that is, contain minimum amounts of impurities. In particular DMF should have an electric conductivity of not more than 1.0 $\mu$ U/cm and the pH of a 20% aqueous solution should be about 6.5 to 8.5.

For the above reasons, in producing DMF by reacting DMA and carbon monoxide, the use of DMA containing unreacted ammonia as a feed, other methylamines, water and so on has been avoided, and high purity DMA has been used as a feed. Hitherto, high purity DMA has been obtained by reacting methanol and ammonia to provide methylamines, isolating DMA from the methylamines, and purifying the DMA. In the reaction of methanol and ammonia, monomethylamine and trimethylamine are inevitably by-produced in addition to DMA as a result of the equilibrium. Among these methylamines, it is DMA that is mainly used in industrial applications. Therefore, surplus monomethylamine and trimethylamine are recycled in the synthesis of methylamines. This leads to installation of a larger scale apparatus for production of DMA which is not in proportion to the production amount of DMA.

In separating DMA from the by-product methylamines, distillation is generally employed. Since these three methylamines, i.e., monomethylamine, DMA, and trimethylamine, and unreacted ammonia form azeotropic mixtures among them, multi-stage distillation is carried out in isolating DMA from the reaction product methylamines.

A typical example of the methods of synthesizing methylamines which are commercially conducted, is described in *Fluid Handling*, January (1963), pp. 13 to 14. According to this method, the reaction product obtained by the catalytic reaction of methanol and ammonia is fed into a first distillation column wherein the unreacted ammonia is withdrawn from the top of the column and recycled to the reaction system. The effluent from the bottom of the column is fed into a second distillation column wherein trimethylamine is isolated from the top of the column by water-extraction distillation; and from the bottom of the column a mixture of DMA, monomethylamine and water is withdrawn. This mixture is fed into a third distillation column wherein the mixture is subjected to dehydration treatment and a mixture of DMA and monomethylamine is withdrawn from the top of the column. The DMA-monomethylamine mixture is introduced into a fourth distillation column wherein the mixture is subjected to an ordinary distillation treatment, monomethylamine is isolated from the top of the column, and DMA is withdrawn from the bottom. The thus obtained high purity DMA is used as a starting material for production of DMF wherein DMA is reacted with carbon monoxide in the presence of an alkali metal alcoholate catalyst such as sodium methylate and the reaction product is distilled and purified to give DMF.

In the prior art DMF production processes as described above, however, the production of DMA is complicated, the operation is troublesome, large quantities of utilities such as steam are consumed, and thus there are many industrial problems which need to be solved.

SUMMARY OF THE INVENTION

A principal object of this invention is to solve the above described defects encountered in the prior art DMF production processes.

A more particular object of this invention is to provide a process for producing DMF which comprises reacting methanol and ammonia to give methylamine and reacting the thus obtained methylamine with carbon monoxide in which the production steps are simplified, the consumption of utilities such as steam is reduced, and the constant production of high quality DMF is possible, and thus to provide a process which is greatly advantageous from an industrial standpoint.

This object is attained by employing a procedure in which the reaction product of methanol and ammonia is subjected to a first distillation treatment to remove unreacted ammonia and monomethylamine as an azeotropic mixture with trimethylamine, the residual mixture is subjected to a second distillation treatment to remove water and to obtain a mixture of DMA and trimethylamine and then the mixture of DMA and trimethylamine is reacted with carbon monoxide.

Accordingly this invention provides a process for producing dimethylformamide which comprises the following steps (a) through (d).

(a) Methanol and ammonia are reacted in a methylamine synthesizing column in the presence of a dehydration catalyst to produce a mixture of mono-, di- and trimethylamines.

(b) The reaction mixture containing mono-, di- and trimethylamine is introduced into a first distillation column wherein unreacted ammonia and monomethylamine is distilled as an azeotropic mixture with trimethylamine to obtain a mixture mainly composed of dimethylamine, trimethylamine and water.

(c) The mixture mainly composed of dimethylamine, trimethylamine and water is introduced into a second distillation column wherein water containing several high boiling point components is removed to obtain a mixture of dimethylamine and trimethylamine.

(d) The mixture of dimethylamine and trimethylamine is introduced into a dimethylformamide synthesizing column wherein dimethylamine is reacted with carbon monoxide in the presence of a catalyst, and unreacted carbon monoxide and trimethylamine are separated to provide dimethylformamide.

BRIEF DESCRIPTION OF THE DRAWING

The FIGURE illustrates a flow diagram showing one embodiment of this invention.

DETAILED DESCRIPTION OF THE INVENTION

This invention will now be explained with reference to the embodiment illustrated in the FIGURE.

Starting materials, methanol (1) and ammonia (2), are introduced into a methylamine synthesizing column A, together with unreacted ammonia and amines (4) recycled from a first distillation column B as hereinafter described and amines (3) recycled from a DMF synthesizing column D and a DMF purification unit F as hereinafter described. They are reacted in the presence of a dehydration catalyst to form methylamines.

Conventional dehydration catalysts can be used in the process of this invention, particularly, $SiO_2$—$Al_2O_3$, $SiO_2$—MgO, $Al_2O_3$, zeolite and the like.

These materials are preferably fed in such a manner that the atomic ratio of nitrogen to carbon (N/C) in the feed (5) is in the range of about 0.5 to 5.0, preferably about 1.0 to 3.0. When the N/C ratio is less than about 0.5, the proportion of DMA produced is small and moreover, the production of higher amines, olefins and other by-products increases. When N/C is more than about 5.0, although the proportion of DMA produced increases, the amount of unreacted ammonia increases. This leads to an increase in the distillation load on the first distillation column B and an increase in the amount of the unreacted ammonia which is recycled.

In the methylamine synthesizing column A, the reaction is carried out at a temperature of about 300° to 500° C., preferably about 350° to 450° C., and at a pressure of about 5 to 50 kg/cm² G, preferably about 15 to 25 kg/cm² G. When the temperature is less than 300° C., the catalytic activity is low and the amount of unreacted methanol increases. Moreover, the proportion of DMA produced decreases in view of the reaction equilibrium. On the other hand, when the temperature is more than 500° C., the amount of by-products such as nitrogen, carbon monoxide, methane and so on increases, leading to an increase in the loss of feed. Simultaneously, the life of the catalyst is shortened.

When the pressure in methylamine synthesizing column A is less than about 5 kg/cm² G, the reaction rate is small and a large quantity of catalyst is needed for obtaining the same conversion. The reaction product should be transferred under pressure to the subsequent purification unit. On the other hand, when the pressure is more than about 50 kg/cm² G, it is necessary to increase the pressure resistance of the reactor and the power to recycle from the purification units.

The thus obtained reaction product (6) contains mono-, di- and trimethylamine and water.

The reaction product (6) is introduced into a first distillation column B at an intermediate location in many cases at the middle position or location slightly above the middle position and in more detail at a position about 20 to about 50%, preferably about 25 to about 35% of the length from the top of the first distillation column, wherein it is distilled. In the upper portion of the first distillation column B, an azeotropic mixture of ammonia, monomethylamine and trimethylamine is formed and distilled from the top of the column. This azeotropic mixture is preferably distilled in such a manner that it contains about 1% of DMA contained in the reaction product (6) to ensure that the monomethylamine is completely removed and not transferred to the subsequent steps. Thus, the bottom effluent (7) is mainly a mixture of DMA, trimethylamine and water.

As the first distillation column B, conventional distillation columns such as a packed column and a tray column can be employed. In employing a tray column, a tray column having a plate number of 40 to 150 is preferred.

The operation pressure in the first distillation column B is about 10 to 30 kg/cm² G, preferably about 15 to 25 kg/cm² G. When the operation pressure in the first distillation is about 10 to 30 kg/cm² G, the temperatures for the top and the bottom of the distillation column are about 40° C. to 80° C. and about 110° C. to 160° C., respectively. When the operation pressure is about 15 to 25 kg/cm² G, the temperatures at the top and the bottom of the distillation column are about 50° C. to 70° C. and about 125° C. to 150° C., respectively.

When the pressure in the first distillation column is less than about 10 kg/cm² G, an azeotropic mixture of DMA and trimethylamine is formed and a large quantity of DMA is contained in the effluent from the top of the column. On the other hand, when the pressure is more than about 30 kg/cm² G, no azeotropic mixture of monomethylamine and trimethylamine is formed. Therefore, to distill off ammonia and monomethylamine at the same time using one distillation column, a large quantity of DMA is inevitably removed. This leads to a reduction in the proportion of DMA in the bottom effluent (7).

The unreacted ammonia and amines (4) distilled off from the first distillation column B can be returned to the methylamine synthesizing unit A wherein they are used as part of a feed for production of methylamine.

The bottom effluent (7) is introduced into a second distillation column C at an intermediate location in many cases at the middle position or at a location slightly above the middle position, in more detail at a position of about 20 to about 60%, preferably about 30 to about 50% of the column length from the top of the second distillation column, wherein the bottom effluent (7) is subjected to dehydration distillation. From the bottom of the column, water and a small amount of high boiling point components, which have been produced during the synthesis of methylamines, are withdrawn, and a mixture of DMA and trimethylamine (9) is removed from the top of the column.

As the second distillation column C, conventional distillation columns such as a packed column and a tray column can be employed. In employing a tray type column, a tray column having a plate number of about 30 to 80 is preferred.

The operation pressure in the second distillation column is atmospheric pressure to 30 kg/cm² G, preferably about 5 to 15 kg/cm² G. When the operation pressure is the atmospheric pressure to 30 kg/cm² G, the temperatures for the top and the bottom of the distillation column are about 5° C. to 135° C. and about 100° C. to 230° C., respectively. When the operation pressure is about 5 to 15 kg/cm² G, the temperatures at the top and the bottom of the distillation column are about 60° to 100° C. and about 155° to 195° C., respectively.

When the operation pressure is less than atmospheric pressure, the temperature in the top of the column decreases below about 5° C. and ordinary cooling water can not be used. Although brine may be employed, it is necessary to increase the heat transfer area of the condenser. On the other hand, when the operation pressure is more than about 30 kg/cm² G, the temperature in the bottom of the column rises above about 230° C. Thus, a high temperature heat source is needed.

The thus obtained DMA-trimethylamine mixture (9) is introduced into a DMF synthesizing column D wherein the mixture is reacted with carbon monoxide (10) in the presence of an alkali alcoholate catalyst (11) by a vapor-liquid contact process. The reaction is preferably carried out under the conditions of a molar ratio of carbon monoxide to DMA (CO/DMA) of about 0.5 to 5.0, preferably about 1.0 to 3.0, a temperature of about ordinary temperature (20° C.) to 200° C., preferably about 100° to 140° C., and a pressure of about 3 to 200 kg/cm² G, preferably about 5 to 30 kg/cm² G. The DMF synthesizing column D is preferably cooled by use of a cooling apparatus inserted therein or an external cooler to control the temperature within the above temperature range suitable for the production of DMF.

A mixed gas (12), in which the major portion of gasified trimethylamine is present, is withdrawn from the top of the synthesizing column D and introduced into a cooler E wherein it is sufficiently cooled to separate the unreacted and inert-gas (13) and, at the same time, trimethylamine is liquidified and recovered.

This trimethylamine can be used itself or it can be returned to the methylamine synthesizing unit A to be converted into DMA.

The DMF produced is recovered as a crude DMF (15) from the top of the synthesizing column D. The crude DMF is introduced into a DMF purification unit F wherein it is purified by distillation (a conventional DMF purification step to separate the high boiling compounds from the mixture). Thus, a high quality DMF (18) is obtained. In this distillation, small amounts of high boiling compounds (17) and a low boiling point mixture (16) containing trimethylamine as a major portion are recovered. The low boiling point mixture may be returned to the methylamine synthesizing unit.

According to the process of this invention, DMA of high purity can be isolated without using such complicated steps as used in the prior art processes, the steps from the production of methylamines to the recovery of DMF are simplified and DMF can be produced in a continuous process, and the quantity of utilities such as consumption of steam and so on are thus markedly reduced.

Using the process of this invention, it is not required for manufacture of DMF to separate intentionally high purity DMA using such complicated steps as in the prior art, and the steps from the production of methylamines to the recovery of DMF are simplified. DMF can be produced in a continuous manner and the quantity of utilities, such as steam consumption, are thus markedly reduced.

Particularly in the purification of methylamines, there are four (4) distillation operations in the prior art. In the process of this invention, however only two (2) distillation operations are required.

In more detail, in the process of this invention, methylamine purification does not require four distillation columns as described in *Fluid Handling*, January 1963 for isolation of high purity DMA. That is, in the first distillation column, ammonia and monomethylamine are separated as an azeotropic mixture from the methylamine synthesis reaction product. Next, water is removed in the second distillation column and the thus obtained DMA-trimethylamine mixture can be employed as a feed for the production of DMF. Therefore, the amounts processed in the second distillation column C can be greatly reduced as compared with the prior art processes. DMA for production of DMF is produced by only two distillation operations, and there is no need of employing special operations for the separation of trimethylamine. This leads to the simplification and minimization of equipment costs, and to a great reduction in the amount of steam and so on used. Moreover, in the process of this invention, no water extraction distillation is needed for separation of trimethylamine as in the prior art process. Only the by-produced water resulting from the formation of methylamine is removed as waste, leading to the reduction of the amounts processed to below one-third that of the prior art process.

In the process of this invention, the mixture of DMA and trimethylamine obtained from the methylamine purification step is directly introduced into the DMF synthesizing column. Therefore, the DMF synthesizing unit itself functions as a trimethylamine concentration and purification unit. Moreover, favorable effects are obtained related to controlling the temperature in the DMF synthesizing column within a predetermined range. In the prior art processes, the cooling of DMF synthesizing column for keeping the temperature therein within the desired range of 100° to 140° C. has been required because the formation of DMF is an exothermic reaction of $\Delta H = 19.8$ Kcal/g-mol. Conversly, in the process of this invention, trimethylamine merely passes through the DMF synthesizing column without participating directly in the reaction in the column, and at this time, it vaporizes, thereby absorbing the heat of reaction. Therefore, there can be obtained the effect of reducing amount of coolant to be used for controlling the temperature which has hitherto been needed in the prior art processes.

As described above, the use of the process of this invention for production of DMF brings about marked effects which could not be obtained by the prior art processes. These effects or advantages of this invention will be summarized below.

(1) As a feed for production of DMF, no DMA of purity is needed and a mixture of DMA and trimethylamine can be employed.

(2) The purification unit of methylamine can be markedly simplified.

(3) The equipment can be minimized.

(4) The amount of waste water processed can be reduced to below one-third that in the conventional process.

(5) Utilities such as steam, cooling water and so on can be greatly reduced as a whole.

(6) The product DMF is not inferior in quality to those DMFs on the market.

Thus, the process of this invention is considered to be quite advantageous for production of DMF.

The following example will be given to illustrate one embodiment of this invention.

EXAMPLE

DMF was produced according to the process illustrated in the FIGURE.

Methanol (359 kg/hr), Ammonia (95 kg/hr), a mixture of ammonia and methylamine withdrawn from the top of the first distillation column B (1245 kg/hr) and a recycle mainly composed of trimethylamine recovered from the DMF synthesizing and purification units (323 kg/hr) were introduced into the methylamine synthesizing column A, which had been filled with a $SiO_2$—$Al_2O_3$ based catalyst, wherein they were reacted at a temperature of 410° C., a pressure of 20 kg/cm$^2$ G and a contact time of 2.2 seconds.

A reaction product (ammonia 42.5%, trimethylamine 21.1%, monomethylamine 13.4%, DMA 12.9%, water 10.0%, methanol 0.1% (herein all % is by weight.)) was obtained. This reaction product was introduced at the 25th position from the top of the first distillation column B having a total plate number of 90 at a rate of 2022 kg/hr wherein it was distilled at a pressure of 18 kg/cm$^2$ G, a reflux ratio of 1.2, a top column temperature of 54° C. and a bottom column temperature of 132° C. From the top of the column B, a mixture of ammonia and methylamines (ammonia 69.0%, monomethylamine 21.8%, trimethylamine 8.5%, DMA 0.7%) was obtained (1245 kg/hr).

The effluent withdrawn from the bottom of the column B was introduced at the 30th position from the top of the second distillation column C having a total plate number of 60 wherein it was distilled at a pressure of 6 kg/cm$^2$ G, a reflux ratio of 1.2, a top column temperature of 53° C. and a bottom column temperature of 157° C. From the top of the column C, a mixture of DMA and trimethylamine (DMA 44.0%, trimethylamine 56.0%) (572 kg/hr) was obtained, and from the bottom water was transferred to a waste water disposal equipment installed outside of the system (not shown).

A mixture of DMA and trimethylamine (572 kg/hr), which had been withdrawn from the methylamine unit, was pressurized by use of a pump, and it was fed to the DMF synthesizing column D and used as a feed for synthesizing DMF. The DMF synthesizing column D was kept at a pressure of 20 kg/cm$^2$ G and a temperature of 120° C., and carbon monoxide 138 Nm$^3$/hr and a catalyst (4.6 kg/hr) (a metanol solution of sodium methylate) were continuously introduced thereinto. A reaction product, crude DMF (DMF 74%, trimethylamine 24.8%, DMA and others 1.2%) was obtained (545 kg/hr).

From the top of the DMF synthesizing column D, the unreacted gas was withdrawn, and it was introduced into a cooler E. Thus, a condensed liquid was obtained (185 kg/hr), and the analysis of the condensed liquid revealed that it was composed of 99.2% trimethylamine. Therefore, it could be used as a product as it was, but it was recycled to the methylamine synthesizing unit and converted into DMA. The uncondensed offgas (unreacted and inert-gas) was transferred to a waste gas disposal equipment (not shown).

The thus obtained DMF reaction product was subjected to ordinary distillation in the purification unit F, and it was separated into a low boiling point component (141 kg/hr) composed mainly of trimethylamine (trimethylamine 95.7%, DMF 0.2%, others 4.1%) and DMF (5 kg/hr) containing a high boiling point component. Thus, the product DMF (399 kg/hr) was obtained.

This product had an electric conductivity of 0.5 $\mu$ U/cm and the pH of a 20% aqueous solution was 7.0. It can be seen that the product DMF obtained by the process of this invention is not at all inferior to those DMFs produced by the prior art processes wherein a high purity DMA is used as a feed.

Furthermore, the amount of the waste water disposed is reduced to less than one-third of the prior art process, and the amount of steam needed mainly in the distillation operation can be reduced by half. The amount of the steam used in the first distillation column was 0.62 ton/hr, 0.12 ton/hr in the second distillation column and 0.48 ton/hr in the purification unit of DMF. The total amount of steam was 1.22 ton/hr, and the amount of waste water was about 205 kg/hr. Conversely, in obtaining the same amount of DMF as obtained in this example by the prior art process, the amount of the steam used was 2.5 ton/hr and the amount of the waste water disposed is about 625 kg/hr.

While the invention has been described in detail and with reference to specific embodiments thereof, it will be apparent to one skilled in the art that various changes and modifications can be made therein without departing from the spirit and scope thereof.

What is claimed is:

1. A process for producing dimethylformamide comprising:

(a) reacting methanol and ammonia in a methylamine synthesizing column in the presence of a dehydration catalyst to produce a mixture of mono-, di- and tri-methylamines;

(b) introducing the reaction product into a first distillation column wherein unreacted ammonia and monomethylamine is distilled as an azeotropic mixture with trimethylamine to yield a mixture composed mainly of dimethylamine, trimethylamine and water;

(c) introducing the mixture of dimethylamine, trimethylamine and water into a second distillation column wherein water containing a small amount of high boiling point components is removed to yield a dimethylamine-trimethylamine mixture; and (d) introducing the dimethylamine-trimethylamine mixture into a dimethylformamide synthesizing column wherein dimethylamine is reacted with carbon monoxide in the presence of a catalyst and unreacted carbon monoxide and trimethylamine are separated to yield dimethylformamide.

2. The process of claim 1 which further comprises introducing the dimethylformamide into a dimethylformamide purification unit wherein it is distilled and purified.

3. The process of claims 1 or 2, wherein the azeotropic mixture distilled from the first distillation column is recycled to the methylamine synthesizing column.

4. The process of claims 1 or 2, wherein the azeotropic mixture distilled from the first distillation column and the trimethylamine obtained from the dimethylformamide synthesizing column are recycled to the methylamine synthesizing column.

5. The process of claim 2, wherein the azeotropic mixture distilled from the first distillation column, and the trimethylamine obtained from the dimethylformamide synthesizing column and the dimethylformamide purification unit are recycled to the methylamine synthesizing column.

6. The process of claims 1 or 2, where in distilling the azeotropic mixture from the first distillation column, the distillation is carried out in such a way that the azeotropic mixture contains about 1% by weight of the dimethylamine contained in the reaction product obtained in the methylamine synthesizing column.

7. The process of claim 1, wherein the nitrogen to carbon ratio in step (a) is about 0.5 to 5.0.

8. The process of claim 1, wherein step (a) is carried out at a temperature of about 300° to 500° C. and a pressure of about 5 to 50 kg/cm$^2$ G.

9. The process of claim 1, wherein said first distillation step (b) is carried out a pressure of about 10 to 30 kg/cm$^2$ G.

10. The process of claim 1, wherein said second distillation (c) is carried out at a pressure of about atmospheric to 30 kg/cm$^2$ G.

11. The process of claim 1, wherein the synthesis of dimethylformamide step (d) is carried out at a temperature of about 20° to 200° C. and a pressure of about 3 to 200 kg/cm$^2$ G.

12. The process of claim 1, wherein the molar ratio of carbon monoxide to dimethylamine is about 0.5 to 5.0 in the dimethylformamide synthesis step (d).

* * * * *